United States Patent
Kim et al.

(10) Patent No.: US 9,616,122 B2
(45) Date of Patent: Apr. 11, 2017

(54) PH SENSITIVE METAL NANOPARTICLE AND PREPARATION METHOD

(75) Inventors: Sung Jee Kim, Pohang-si (KR); Sang Hwa Jeong, Pohang-si (KR); Hyo Kyun Chung, Jung-gu (KR); Ju Taek Nam, Pohang-si (KR); Na Youn Won, Pohang-si (KR)

(73) Assignee: POSTECH ACADEMY-INDUSTRY FOUNDATION, Pohang-si, Gyungbuk (KR)

( * ) Notice: Subject to any disclaimer, the term of this patent is extended or adjusted under 35 U.S.C. 154(b) by 79 days.

(21) Appl. No.: 13/002,476

(22) PCT Filed: Jul. 3, 2009

(86) PCT No.: PCT/KR2009/003640
§ 371 (c)(1),
(2), (4) Date: Apr. 21, 2011

(87) PCT Pub. No.: WO2010/002217
PCT Pub. Date: Jan. 7, 2010

(65) Prior Publication Data
US 2011/0269170 A1 Nov. 3, 2011

(30) Foreign Application Priority Data
Jul. 3, 2008 (KR) ........................ 10-2008-0064270

(51) Int. Cl.
*A61K 41/00* (2006.01)
*A61K 49/00* (2006.01)
*A61K 51/04* (2006.01)
*A61K 47/48* (2006.01)
*A61K 51/12* (2006.01)
*B82Y 5/00* (2011.01)

(52) U.S. Cl.
CPC ...... *A61K 41/0052* (2013.01); *A61K 47/4813* (2013.01); *A61K 49/0065* (2013.01); *A61K 51/0402* (2013.01); *A61B 2562/0285* (2013.01); *A61K 51/1255* (2013.01); *B82Y 5/00* (2013.01)

(58) Field of Classification Search
None
See application file for complete search history.

(56) References Cited

U.S. PATENT DOCUMENTS

| | | | |
|---|---|---|---|
| 5,373,093 A * | 12/1994 | Vallarino et al. | 534/15 |
| 2002/0103517 A1* | 8/2002 | West et al. | 607/88 |
| 2006/0099146 A1 | 5/2006 | Chow et al. | |

FOREIGN PATENT DOCUMENTS

| WO | 2005/029076 A2 | 3/2005 |
|---|---|---|
| WO | 2007/097605 A1 | 8/2007 |
| WO | 2008/010687 A1 | 1/2008 |

OTHER PUBLICATIONS

Mok, H., et al., "Enhanced Intracellular Delivery of Quantum Dot and Adenovirus Nanoparticles Triggered by Acidic pH via Surface Charge Reversal", 2008, Bioconjugate Chemistry, pp. 797-801.*
Dixit, V., et al., "Synthesis and Grafting of Thioctic Acidâ´-PEGâ´Folate Conjugates onto Au Nanoparticles for Selective Targeting of Folate Receptor-Positive Tumor Cells", 2006, Bioconjugate Chemistry, pp. 603-608.*
Lee, Yan, "A Protein Nanocarrier from Charge-Conversion Polymer in Response to Endosomal pH", 2007, JACS, pp. 5362-5363.*
Glycanaid, "Glycanaid", accessed from: http://glycanaid.com/GlycanAid_Product_Sheet.pdf, printed on : Nov. 30, 2013.*
Mitchell, G.P., et al., "Programmed Assembly of DNA Functionalized Quantum Dots", 1999, JACS, pp. 8122-8123.*
Jaskolski, W., et al., "Coupling and Strain Effects in Vertically Stacked Double InAs/GaAs Quantum Dots: Tight-Binding Approach", 2004, Acta Physica Polonica A, pp. 193-205.*
El-Sayed, I.H., et al., "Surface Plasmon Resonance Scattering and Absorption of anti-EGFR Antibody Conjugated Gold Nanoparticles in Cancer Diagnostics: Applications in Oral Cancer", 2005, Nano Letters, pp. 829-834.*
Mayya, K.S. et al., On the Stability of Carboxylic Acid Derivatized Gold Colloidal Particles: The Role of Colloidal Solution pH Studied by Optical Absorption Spectroscopy, 1997, Langmuir, pp. 3944-3947.*
Shipway, A.N., et al., "Investigations into the Electrostatically Induced Aggregation of Au Nanoparticles", 2000, Langmuir, pp. 8789-8795.*
Selvakannan, PR.S., "Capping of Gold Nanoparticles by the Amino Acid Lysine Renders Them Water-Dispersible", Langmuir, 2003, pp. 3545-3549.*
Carofiglio, T., et al., "Synthesis, characterization and chemisorption on gold of a -cyclodextrin—lipoic acid conjugate", Tetrahedron, 2001, pp. 5241-5244.*
Gaidamauskas, E., et al., "Deprotonation of b-cyclodextrin in alkaline solutions", 2009, Carbodyhrate, 2009, pp. 250-254.*
International Search Report, International Application No. PCT/KR2009/003640.

(Continued)

*Primary Examiner* — Michael G Hartley
*Assistant Examiner* — Lance Rider
(74) *Attorney, Agent, or Firm* — Steptoe & Johnson LLP

(57) ABSTRACT

The present invention relates to a pH sensitive particle, a method of preparation thereof, and a use thereof. More particularly, the invention provides a pH sensitive metal nanoparticle and its use for medical treatment utilizing cell necrosis during photothermal therapy. The pH sensitive metal nanoparticle based on this invention consists of a pH sensitive ligand compound whose charge changes depending on the pH of the metal nanoparticle. The particle can be collected in cells, such as cancer cells which present an abnormal pH environment. The pH sensitive metal nanoparticle based on this invention can induce cell death through a photothermal procedure after aggregation. Therefore, the invention enables medical treatment using cell necrosis for e.g. cancer treatment.

23 Claims, 6 Drawing Sheets

(56) References Cited

OTHER PUBLICATIONS

Shim, J-Y, et al. (2007) "Reversible aggregation of gold nanoparticles induced by pH dependent conformational transitions of a self-assembled polypeptide." *Journal of Colloic and Interface Science*, 316, 977-983.

Diagaradjane, P., et al. (2008) "Modulation of in vivo tumor radiation response via gold nanoshell-mediated vascular-focused hyperthermia: characterizing an integrated antihypoxic and localized vascular disrupting targeting strategy." *Nano Letters*, vol. 8, No. 5, 1492-1500.

Nuopponen, M., et al. (2007) "Gold nanoparticles protected with pH and temperature-sensitive diblock copolymers." *Langmuir*, 23, 5352-5357.

Zheng, P., et al. (2006) "Formation of gold@polymer core—shell particles and gold particle clusters on a template of thermoresponsive and pH-responsive coordination triblock copolymer." *Langmuir*, 22, 9393-9396.

Han, X., et al. (2008) "A general strategy toward pH-controlled aggregation-dispersion of gold nanoparticles and single-walled carbon nanotubes." *Small*, vol. 4, No. 3, 326-329.

European Communication pursuant to Article 94(3) EPC dated May 10, 2016, issued in EP Application No. 09 773 753.0.

Oishi, Motoi, et al., "One-Pot Synthesis of pH-Responsive PEGylated Nanogels Containing Gold Nanoparticles by Autoreduction of Chloroaurate Ions within Nanoreactors," *Macromol. Chem. Phys.* 2007, 208, 1176-1182.

EPO Search Report for Application No. 09773753.0 mailed Nov. 13, 2014.

\* cited by examiner

PH SENSITIVE METAL NANOPARTICLE AND PREPARATION METHOD

TECHNICAL FIELD

The present invention relates to a pH-sensitive particle, a method for the preparation thereof, and the use thereof. More particularly, the present invention relates to a pH-sensitive metal nanoparticle, a method for the preparation thereof, and the use thereof in medical treatment utilizing cell death through photothermal therapy.

BACKGROUND ART

Environments around abnormal cells such as cancer cells are known to be weakly acidic with a pH of 6.0 to 7.2, unlike the normal body environment which ranges in pH from 7.2 to 7.4. Therapies for cancer using this property are under study.

Korean Patent No. 802080, issued to the Sungkyunkwan University Foundation for Corporate Collaboration, discloses a pH-sensitive copolymer consisting of biodegradable poly(β-aminoester) and hydrophilic polyethylene glycol, which can form micelle structures due to their own amphiphilicity and pH-dependent ionization, whereby the micelles can deliver drugs to cancer cells depending on the change in pH and kill the cells.

WO 2002/20510 discloses novel acid-sensitive compounds comprising an acid-sensitive cyclic ortho-ester and at least one hydrophilic substituent, and their salts. The compounds form conjugates (liposomes, complexes, nanoparticles, etc.) with therapeutic molecules so as to release the therapeutic molecule in cell tissues or compartments where the pH thereof is acidic.

Plasmons play a large role in the optical properties of metals. Surface plasmons are the collective oscillations of free electrons of a metal surface on which light is incident, which take place due to resonance with electromagnetic waves of specific energy that propagate in a direction parallel to the metal/dielectric (e.g., air, water) interface. Because the interactions between light and metal nanoparticles are so strong, the metal nanoparticles show very large coefficients of absorption at resonant frequencies compared to organic dyes. In addition, the resonant frequency of metal nanoparticles varies depending on various factors including size, morphology, kinds of solvents in which they are suspended, etc. Thus, a lot of efforts have been being made into applying various metal nanoparticles to optical sensors or condensers by modifying them in terms of size, morphology, and surface properties.

Recently, metal nanoparticles have been becoming popular because of the possibility of their being used in photothermal therapy thanks to the light-harvesting effect thereof. Photothermal therapy is a use of light energy in the form of thermal energy and is used to treat various medical conditions, including cancer. The light collected on the surface of gold nanoparticles is emitted by various processes, including electron-lattice vibrations, and electron-electron scattering, with the concomitant production of heat. In consideration of the great light-harvesting effect and large surface area-to-volume of gold nanoparticles, the thermal energy locally emitted from the gold nanoparticles is sufficient to cause cell death. Further, because cancer cells are highly vulnerable to heat compared to normal cells, the heat emitted from gold nanoparticles on which light is focused at a controlled intensity can be locally introduced to selectively kill cancer cells without damaging normal cells.

Korean Patent Application No. 2006-102604 discloses a core-shell particle consisting of a silica core 50-500 nm in size, and a gold shell embedded with magnetic nanoparticles, with cancer cell-targeting ligands bonded to the gold shell. The core-shell particle is useful for the diagnosis and magnetic resonance imaging of cancer by taking advantage of the magnetic nanoparticles attached to cancer cells via the cancer cell-targeting ligands. Further, the heat released from the gold nanoshell absorbing the energy of electromagnetic pulses in the near infrared ray range can be used to selectively destroy cancer cells. However, problems with the core-shell particle structure include that of the development of biological ligands for effectively detecting specific cancer cells and conjugating them to the metal.

There is therefore a need for metal nanoparticles that can selectively detect various cancer cells.

DISCLOSURE

Technical Problem

It is an object of the present invention to provide a novel pH-sensitive particle.

It is another object of the present invention to provide a pH-sensitive metal nanoparticle.

It is a further object of the present invention to provide a method for preparing a pH-sensitive metal nanoparticle.

It is still a further object of the present invention to provide a method for destroying abnormal cells using the pH-sensitive particle.

It is still another object of the present invention to provide a novel pH-sensitive compound.

It is yet another object of the present invention to provide a method for synthesizing a novel pH-sensitive compound.

It is yet a further object of the present invention to provide the use of the pH-sensitive particle as a sensor.

Technical Solution

In accordance with an aspect of the invention, the present invention pertains to metal nanoparticles each of which having compounds on its surface, wherein the charge of the compound changes depending on pH.

In an embodiment of the present invention, the metal nanoparticle may be a metal particle itself or a core material, such as silica, coated with metal. The metal may be a pure metal or an alloy which can bond to a compound whose charge changes depending on pH. Preferably, the metal is gold.

The compound of the present invention, which changes its charge depending on pH, can bond to an exposed atom of the metal nanoparticle.

It is preferable that the compound changes its charge at pH 7.0. In an embodiment, the compound may change its charge from negative under a neutral or alkaline environment to positive under an acidic environment.

In accordance with the present invention, the compound, the charge of which changes depending on pH, can be represented by the following Chemical Formula I:

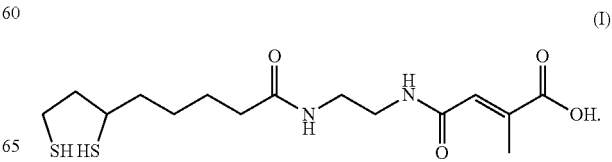

The pH-sensitive metal nanoparticle according to the present invention can be prepared by attaching a compound varying in charge with pH to the surface of the metal nanoparticle.

It should be understood that any metal nanoparticle may be used in the present invention if a compound which varies in charge with pH can be attached to it. In a preferred embodiment, the metal particle is a gold particle or a gold-M coated particle to which the sulfur atom of the compound can bind. In a preferred embodiment, the compound varying in charge with pH is represented by the following Chemical Formula I:

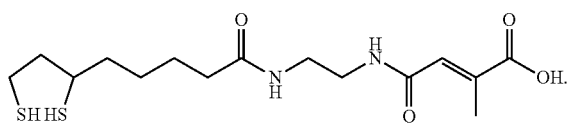

(I)

In an embodiment, the compound the charge of which changes with pH may be introduced onto the metal nanoparticles by substitution with a ligand attached to the surface of the nanoparticles, for example, citrate for stabilizing the gold nanoparticles.

In accordance with an aspect thereof, the present invention pertains to medical photothermal therapy which comprises administering pH-sensitive metal nanoparticles to aggregate, and irradiating the aggregated metal nanoparticles with light to destroy abnormal cells.

In an embodiment, the abnormal cells are cells which present a pH environment different from the normal body environment. For example, the abnormal cells are cancer cells presenting an acidic pH environment.

The pH-sensitive metal nanoparticle is prepared preferably from a metal which can receive light from a light source outside of cells to destroy cells as a result of a photothermal process. So long as it is typically employed in photothermal therapy, any metal particle may be used in the present invention. Preferable are gold particles.

In a preferred embodiment, the metal nanoparticle is small enough to penetrate into abnormal cells. In the present invention, the metal nanoparticle is less than 20 nm in diameter and preferably ranges in diameter from 5 to 15 nm.

In the present invention, once the metal nanoparticles access and/or penetrate into abnormal cells, the metal nanoparticles aggregate in the cells presenting the acidic pH environment, and therefore the aggregated metal nanoparticles are restrained from be released from the cells. In such a situation, the aggregated nanoparticles can be used for photothermal therapy, resulting in the destruction of the cells.

As described above, the metal nanoparticles of the present invention are pH-sensitive particles, which can detect and aggregate at the low pH typical of abnormal cells, such as cancer cells.

In an embodiment of the present invention, the metal nanoparticles may be in the form of having compounds on their surfaces, wherein the compounds aggregate in an acidic pH environment.

When the environment of the metal nanoparticles is changed from alkaline to acidic, at least a portion of the compounds on the surface of the metal nanoparticles are hydrolyzed to give them a charge different from that which they has under an alkaline environment. During the charge change, the particles aggregate to each other due to electrostatic attraction.

Surprisingly, the wavelength of light absorbed by the pH-sensitive metal nanoparticles becomes longer as they aggregate. Thus, the metal nanoparticles, whether aggregating at subcutaneous regions or within deep body regions such as organs, can emit heat when long-wavelength light, such as infrared light, is applied thereto. That is, the metal nanoparticles of the present invention allow photothermal therapy to be conducted at any region where there is cancer, thus extending the application range of photothermal therapy.

In accordance with an aspect thereof, the present invention pertains to a pH-sensitive compound represented by the following chemical formula I:

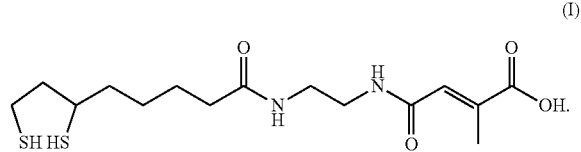 [SMILES: C/C(=C\C(=O)NCCNC(=O)CCCCC(S)CCS)C(=O)O]

(I)

In accordance with an aspect thereof, the present invention pertains to a method for preparing a pH-sensitive compound represented by the following chemical formula I:

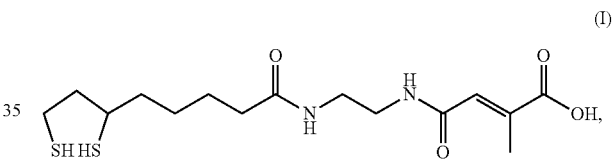

(I)

comprising:

reacting lipoic acid with ethylene diamine to produce a compound represented by the following chemical formula II:

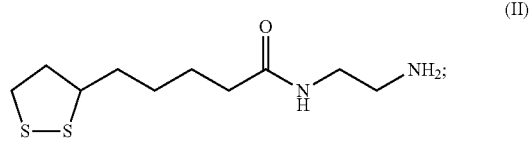 [SMILES: NCCNC(=O)CCCCC1CCSS1]

(II)

reacting the compound of chemical formula II with citraconic anhydride to give a compound represented by the following chemical formula III:

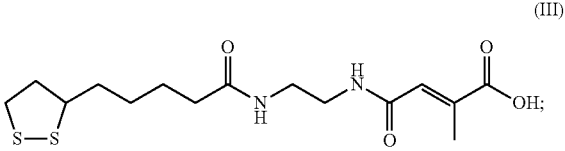 [SMILES: C/C(=C\C(=O)NCCNC(=O)CCCCC1CCSS1)C(=O)O]

(III)

and reacting the compound of chemical formula III with sodium borohydride to give the compound of chemical formula I.

Having the properties of aggregating only at the cells presenting an abnormal pH environment, such as cancer cells, and absorbing long-wavelength light, the pH-sensitive particles of the present invention find use in various applications. For example, the pH-sensitive particles of the present invention may be used in reagents for cancer diagnosis, contrast agents, cancer therapeutics, photosensitizers, etc. When they are associated with a sensor, the pH-sensitive nanoparticles may be used to monitor pH changes.

In accordance with an aspect thereof, the present invention pertains to an aggregate of infrared-absorbing, gold nanoparticles having 5-20 nm in diameter. The aggregate is in the form of clusters, each ranging in diameter from 0.1 to 10 microns and preferably from 1 to 3 microns.

In accordance with an aspect thereof, the present invention pertains to a method for heating the aggregated gold nanoparticles by irradiating them with infrared light.

The pH-sensitive gold nanoparticles of the present invention are well dispersed and absorb only a band of wavelengths below 600 nm under neutral or basic conditions. In contrast, when they are under an acidic condition, their surface charges change and thereby the pH-sensitive gold nanoparticles aggregate to each other due to electrostatic attraction. The absorption band of the nanoparticle aggregates thus formed shifts from 600 nm or less to greater than 600 nm, that is, the longer wavelength band of visible light or the infrared band, due to the surface plasmons thereof.

For applications to photothermal therapy that induce cancer cell death, the pH-sensitive gold nanoparticles, when injected into cancer tissues, form aggregates in a site-specific manner in cancer cells because of the acidic environment of cancer cells. In addition, the nanoparticles introduced into cancer cells are induced to aggregate at intracellular acidic organelles such as endosomes. Because they form aggregates within cells, the pH-sensitive gold nanoparticles introduced into cancer cells inhibit exocytosis and are difficult to release from the cells, allowing an expectation to be formulated that they will be efficient in anticancer therapy. One of the greatest advantages of photothermal therapy based on the pH-sensitive gold particles is that the absorption wavelength of aggregates of the pH-sensitive gold nanoparticles introduced into cancer cells shifts towards longer wavelengths due to surface plasmons. Hence, the wavelength shift leads to the use of long-wavelength light which can penetrate deeply into the body, allowing the application of the pH-sensitive gold nanoparticle-based photothermal therapy to cancer tissues located in regions deep beneath the skin. Conventional photothermal therapy suffers from the disadvantage of being applicable only to cancer occurring at places a short distance from the skin, such as skin cancer, because its photosensitizers respond to short-wavelength light that cannot penetrate deeply into the body. This drawback can be overcome by the pH-sensitive gold nanoparticles. In addition, only when forming aggregates, the pH-sensitive gold nanoparticles can absorb energy from a light source of long wavelengths, thereby guaranteeing the highly selective destruction of cancer cells. The light absorption bands of conventional photosensitizers for photothermal therapy do not shift and thus are inferior in selectivity to the particles of the present invention.

In accordance with an aspect thereof, the present invention pertains to metal nanoparticles which have an average diameter of from 1 to 500 nm, comprise pH-sensitive compounds thereon, and aggregate at an acidic pH environment.

In an embodiment of the present invention, the pH-sensitive compound may be a polymer and/or a low-molecular weight compound well-known in the art. The compound may be introduced onto the metal particles using a well-known process, for example, coating, e.g. spray coating, substitution, e.g., ligand substitution, or mixing, e.g., mixing metal power with compound powder. So long as it allows the metal particles to aggregate at an acidic pH environment, any pH-sensitive compound may be introduced on the metal particles without limitation.

Advantageous Effects

Aggregating in cells presenting an abnormal pH environment, as described hitherto, the pH-sensitive metal nanoparticles prepared according to the methods of the present invention can find applications in various fields, including cancer therapy and diagnosis.

BEST MODE

Examples

Synthesis of pH-Sensitive Ligand

Figure 1:
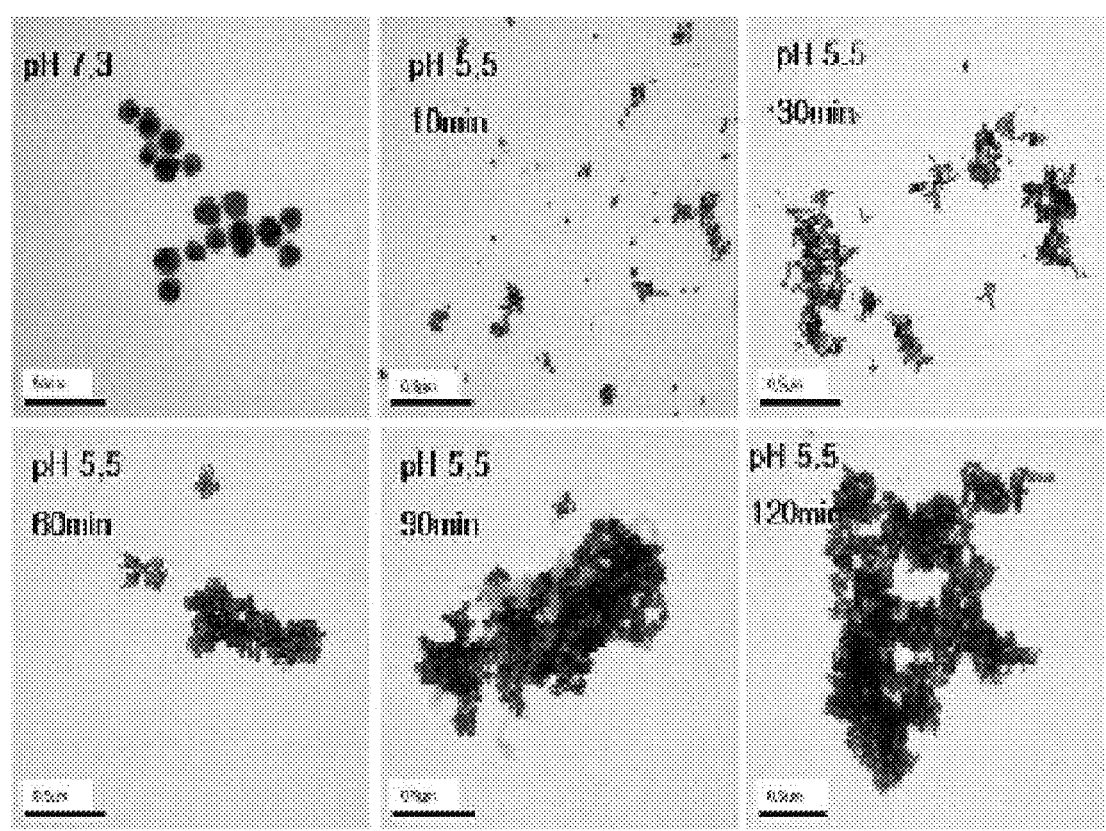
FIG. 1 is of transmission electron microphotographs showing the pH-sensitive gold nanoparticles of the present invention which are dispersed in an aqueous solution at pH 7.3 and at pH 5.5 with the lapse of 10 min, 30 min, 120 min, 90 min and 60 min, respectively (from the left upper panel in a clockwise direction) (scale bars represent 50 nm for pH 7.3 and 500 nm for pH 5.5).

A solution of lipoic acid (1) in anhydrous chloroform, as illustrated in the following reaction scheme, were first mixed at room temperature for 5 min with 1.3 equivalents of carbonyldiimidazole under a vacuum condition with stirring, followed by separating the reaction solution layer from the remaining carbonyldiimidazole. Ethylenediamine was dissolved in an amount corresponding to 5 equivalents of the lipoic acid in anhydrous chloroform under a nitrogen atmosphere, cooled in an ice bath, and mixed for 1 hr with the separated reaction solution by stirring. The resulting reaction solution containing the product (2) was extracted three times with 10% NaCl and once with deionized water and mixed at room temperature for 24 hrs with citraconic anhydride to form a solid substance (3). After filtration, the solid substance was dissolved in an aqueous solution which was adjusted to a pH of 9 with NaOH. The resulting solution was stirred at room temperature for 4 hrs along with 1 equivalent of NaBH$_4$ to afford a pH-sensitive ligand (4) which was used without further purification.

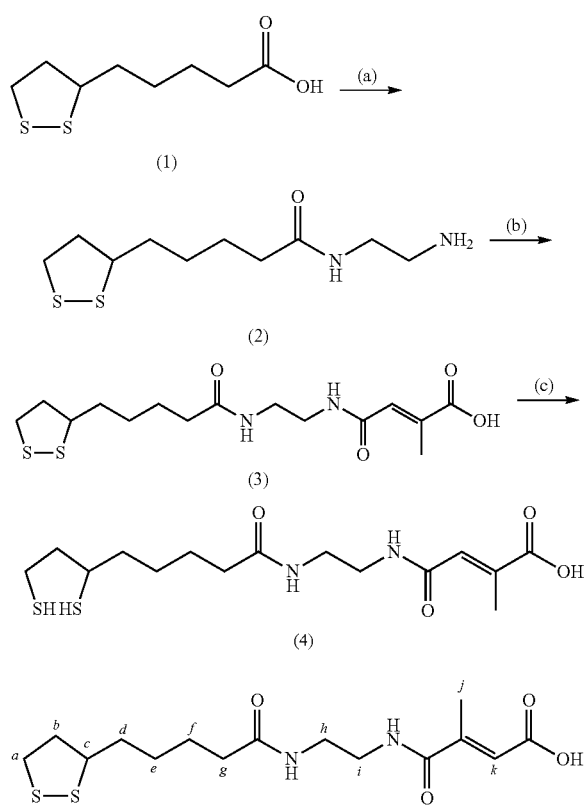

(D$_2$O); δ 1.40 (p, 2H; e), δ 1.55-1.80 (m, 4H; d, f) δ 1.90-2.05 (m, 4H; b, j), δ 2.25 (t, 2H; g), δ 2.40-2.55 (m, 1H; b), δ 3.10-3.30 (m, 2H; a), δ 3.32 (s, 4H; h, i), δ 3.65-3.75 (m, 1H; c), δ 5.57 (s, 1H; k)

(4)

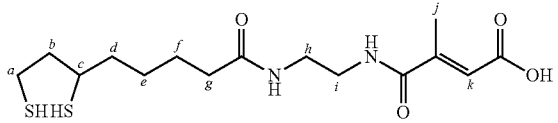

(D$_2$O); δ 1.35-1.75 (m, 7H; b, d, e, f), δ 1.75-1.95 (m, 1H; b) δ 2.00 (s, 3H; j), δ 2.28 (t, 2H; g), δ 2.50-2.70 (m, 2H; a), δ 2.85-2.95 (m, 1H; c), δ 3.34 (s, 4H; h, i), δ 5.62 (s, 1H; k)

[s: singlet, t: triplet, p: pentet, m: multiplet]

Under an acidic condition, the product (4) is hydrolyzed at its amide bond into a primary amine and citraconic acid, as illustrated in the following reaction scheme. The primary amine is positively charged at an acidic pH.

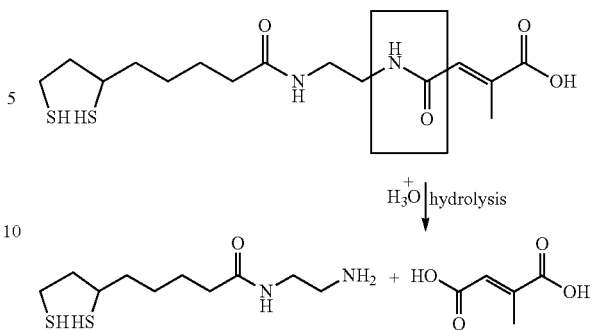

Synthesis of Gold Nanoparticles Stabilized with Citrate

Figure 5:
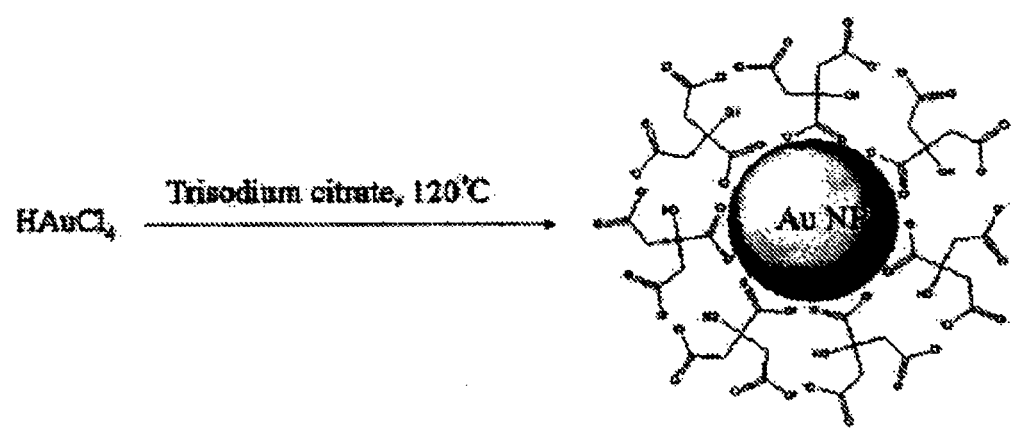
FIG. 5 depicts synthesis of gold nanoparticles stabilized with citrate.

A solution of the gold precursor HAuCl$_4$ in distilled water was heated at 120° C. for 30 min with stirring, and then for an additional 2 hrs along with trisodium citrate with stirring. In this regard, while the trisodium citrate acted as a reducing agent and a surface ligand, the solution turned from yellow to red, indicating the construction of gold nanoparticles. Afterwards, the solution was cooled at room temperature with stirring. (*Ind. Eng. Chem. Res.* 2007, 46, 3128-3136). See FIG. 5.

Synthesis of pH-Sensitive Gold Nanoparticles

Figure 6:
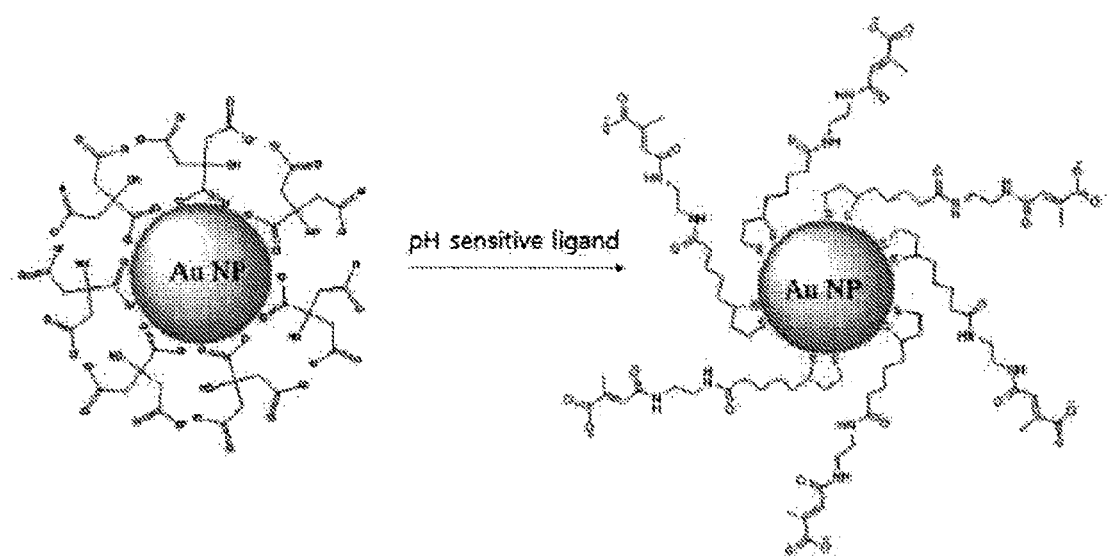
FIG. 6 depicts synthesis of pH-Sensitive gold nanoparticles.

To an aqueous solution containing an excess of the synthetic pH-sensitive ligand were added the citrate-stabilized gold nanoparticles, followed by stirring at room temperature for 8 hrs. Because the dithiol of the pH-sensitive ligand binds more strongly to the surface of the gold nanoparticles than does the carboxylic acid of citrate, the pH-sensitive ligand is exchanged for the citrate. Excess ligands were removed by dialysis. See FIG. 6.

Aggregation Characteristics of pH-Sensitive Gold Nanoparticles

The pH-sensitive gold nanoparticles were dispersed in aqueous solutions at pH 7.3 and pH 5.5, respectively. 10 min, 30 min, 120 min, 90 min, and 60 min after the dispersion, the pH-sensitive gold nanoparticles were observed through transmission electron microimages. The results are given in FIG. 1. As shown in the TEM of FIG. 1, the pH-sensitive nanoparticles were observed to aggregate at pH 5.5. In contrast, the pH-sensitive gold nanoparticles were well dispersed at an average size of 15 nm under a pH 7.3 condition irrespective of the lapse of time. When the condition was changed to a pH of 5.5, the particles formed aggregates which were observed to gradually increase in size to ones of microns with time.

Light Absorption Properties According to Aggregation of Gold Nanoparticles

Figure 2:
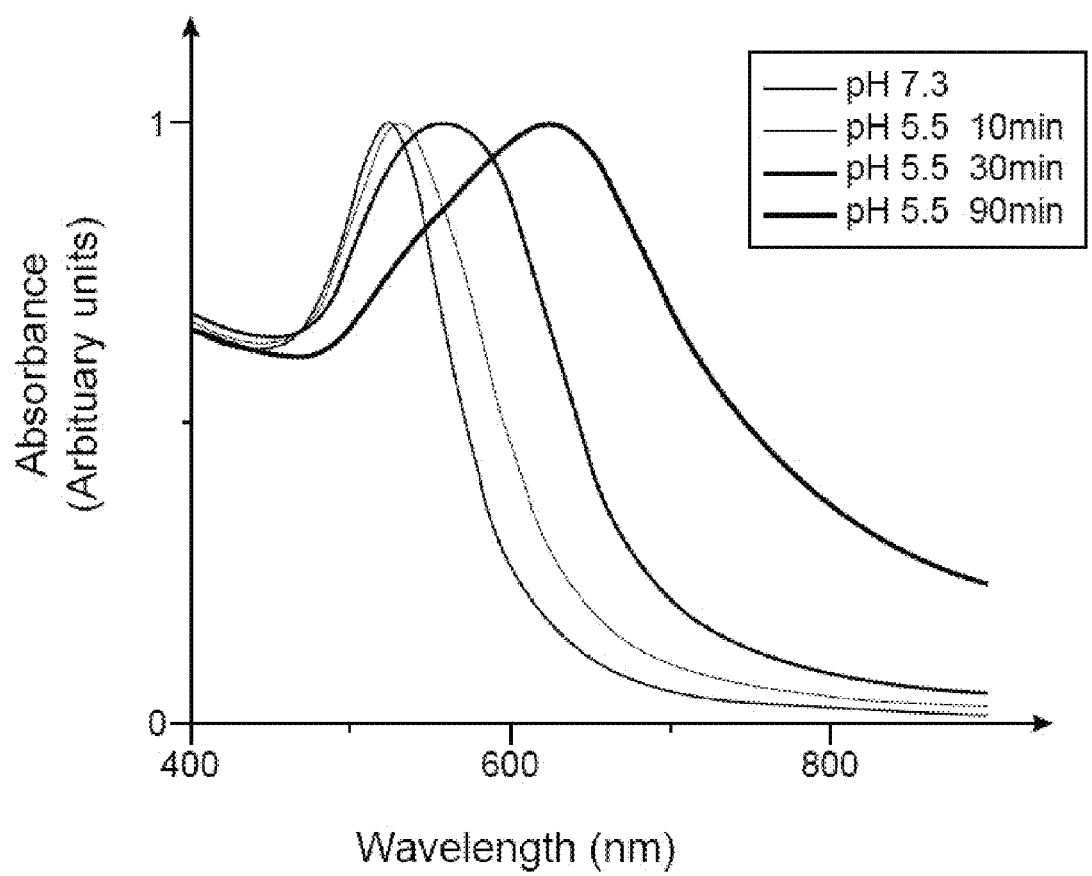
FIG. 2 shows light absorption spectra of the pH-sensitive gold nanoparticles of the present invention according to pH and time. Absorbance was measured 24 hrs after the pH-sensitive gold nanoparticles were dispersed at pH 7.3 (black) and 10 min, 30 min and 90 min after the pH-sensitive gold nanoparticles were dispersed in an acetate buffer solution at pH 5.5 (blue, green and red, respectively).

After being exposed to a pH of 7.3 and 5.5 similar respectively to the surrounding conditions of normal cells and cancer cells, the light absorption of the synthetic pH-sensitive gold nanoparticles was measured over time. Light absorption spectra of the synthetic pH-sensitive gold nanoparticles observed 24 hrs after dispersion under a pH 7.3 condition and 10 min, 30 min and 90 min after dispersion under a pH 5.5 condition are depicted in FIG. 2.

At pH 7.3 corresponding to a normal biological condition, the pH-sensitive gold nanoparticles were found to intensively absorb only a band of visible light less than 600 nm, but when the condition was adjusted to pH 5.5, their absorption wavelength was observed to shift toward longer wavelengths with time and finally to the red-near infrared ranges. This is attributed to the fact that the pH-sensitive gold nanoparticles aggregate to each other thanks to the electrostatic attraction generated while the charge of the surface ligand of the particles changes from positive to negative when hydrolyzed.

The pH-sensitive gold nanoparticles around normal cells which form a neutral environment of pH 7.3~7.4 absorb only light in a visible range of less than 600 nm. In contrast, when around cancer cells which form an acidic condition of pH 5.5, the pH-sensitive gold nanoparticles form aggregates which absorb light in the red-infrared range. In addition to the selective photothermal therapeutic potential of the pH-sensitive gold nanoparticles for cancer, the red-infrared light exhibits the advantage of increasing the photothermal effect of metal nanoparticles because it is only slightly absorbed or scattered by bio-substances such as the skin, blood, etc.

Observation with Dark-Field Microscope

Figure 3:
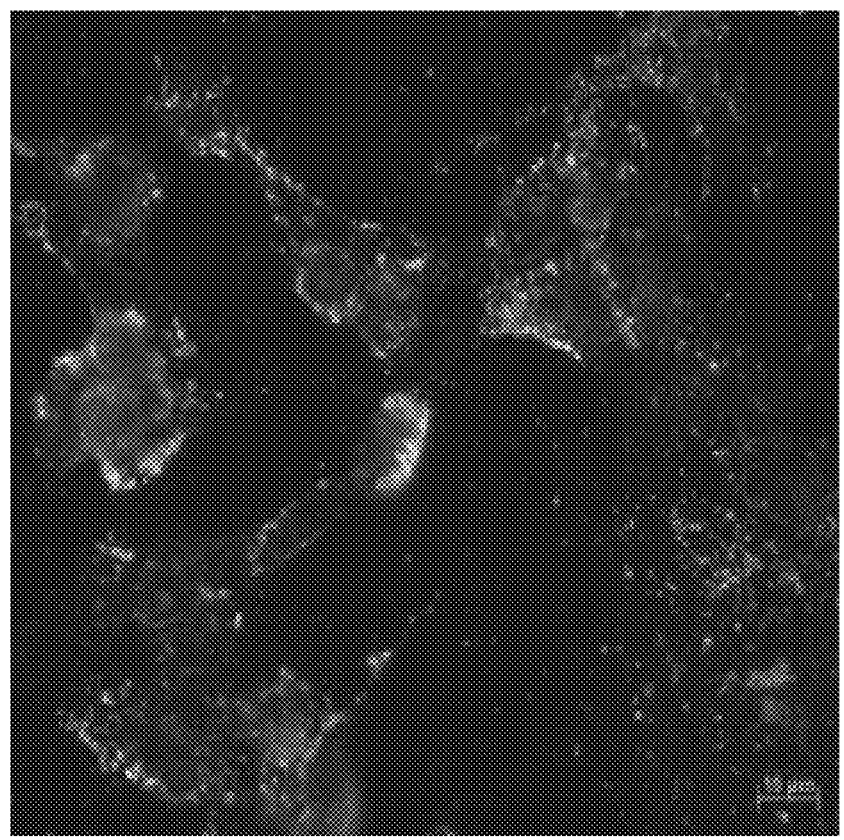
FIG. 3 is a dark-field microphotograph showing the pH-sensitive gold nanoparticles of the present invention captured by uterine cervical cancer cells. The gold nanoparticles which aggregate within the cells are visualized red.

Uterine cervical cancer cells were treated with the pH-sensitive gold nanoparticles before observation with a dark-field microscope. The image photographed by the dark-field microscope is given in FIG. 3. As the gold nanoparticles aggregated, their absorption wavelengths shifted toward longer wavelengths. Thus, because they absorbed red-near infrared light, a red image was observed with a dark-field microscope.

After they are introduced into cells through endocytosis by endosomes, the pH-sensitive gold nanoparticles are exposed to an acidic condition during the fusion of the endosomes with lysosomes and thus form aggregates.

Test for Photothermal Therapy

Figure 4:
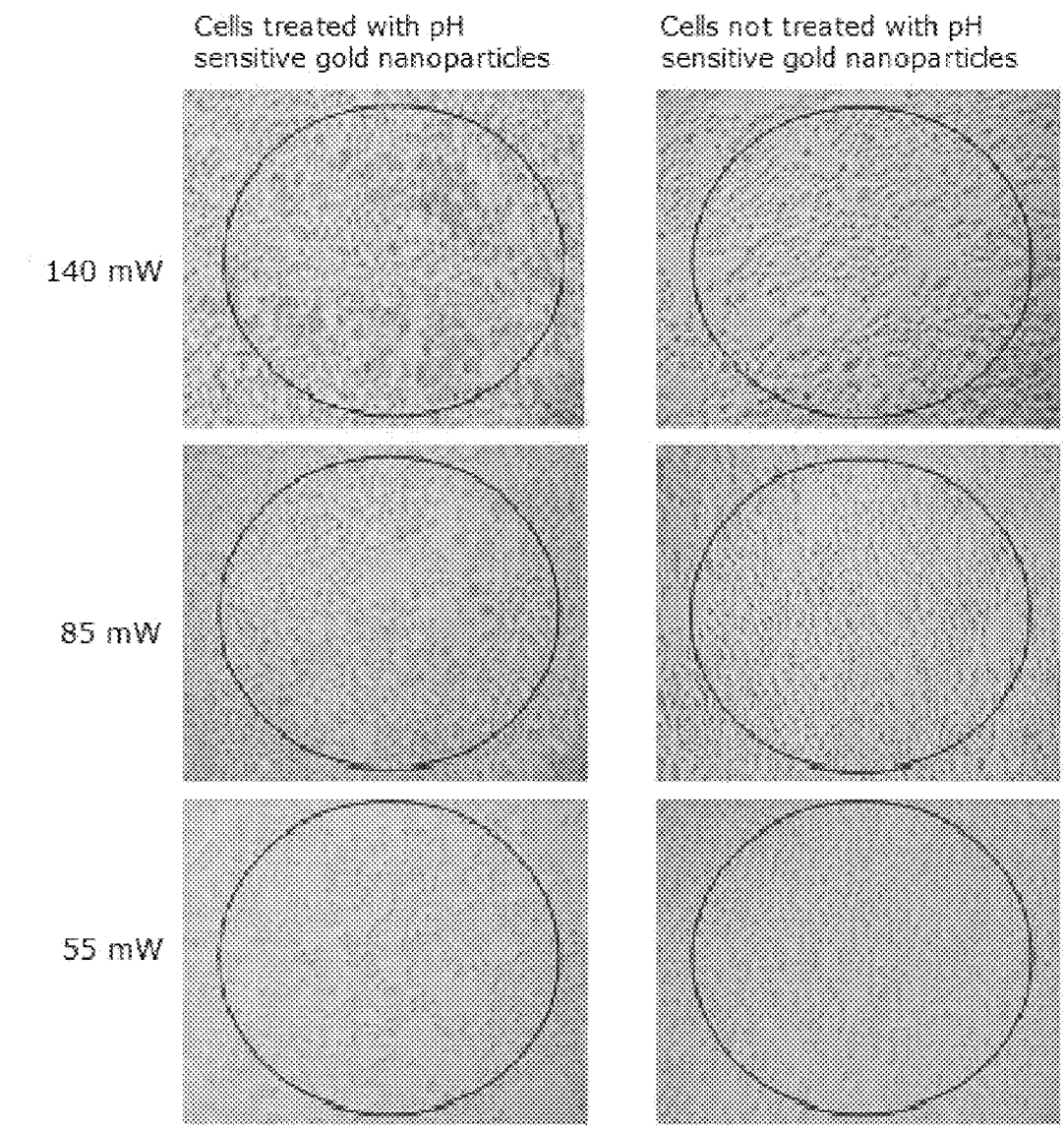
FIG. 4 is of optical photographs showing the cells treated with (left row) and without the pH-sensitive gold nanoparticles of the present invention (right row) after the cells were exposed for 10 min to a laser of 660 nm wavelength at 140 mW (top panels), 85 mW (middle panels) and 55 mW (bottom panels) and stained with trypan blue. The cells killed by the photothermal effect of the pH-sensitive gold nanoparticles are visualized in blue.

Tests for photothermal therapy were conducted in vitro with the pH-sensitive gold nanoparticles. Uterine cervical cancer cells were incubated in combination with pH-sensitive gold nanoparticles to introduce the nanoparticles into the cells (experimental group). For a control, the cells were incubated alone. The experimental group and the control were exposed to a laser of 660 nm for 10 min at a power of 140 mW, 85 mW and 55 mW. Thereafter, the cells were stained with trypan blue before observation under an optical microscope. The images are given in FIG. 4. Irradiated portions are indicated by circles.

Trypan blue selectively stains dead cells. No dead cells were detected in both the experimental group and the control when they were exposed to a laser at a power of 55 mW less than a threshold, indicating that the pH-sensitive gold nanoparticles exhibit no cytotoxicity under a light condition less than the threshold. That is, the pH-sensitive gold nanoparticles of the present invention meet the requirement of therapeutic photosensitizers that are non-toxic under a condition of darkness. When irradiated with a laser with a power of 85 mW, only cells in the experimental group were selectively killed. At a power of 140 mW, the cells of the experimental group were also selectively killed. More cells were killed at a power of 140 mW than at a power of 85 mW, indicating that photothermal therapy induces cell death in a dose-dependent manner. Consequently, the pH-sensitive gold nanoparticles of the present invention can be useful in the photothermal therapy of cancer.

The invention claimed is:

1. Metal nanoparticles each of which have a compound on their surface, wherein the charge of the compound changes depending on pH, the compound is represented by the following chemical formula I:

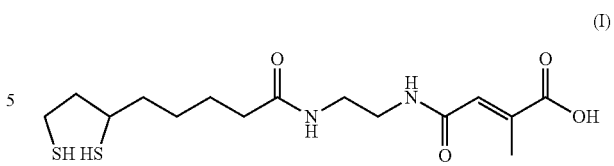

the metal nanoparticles aggregate to each other due to electrostatic attraction as the charge of the compound changes, the compound changes in net charge after undergoing hydrolysis, and the metal nanoparticles absorb a light in the red-infrared range after aggregation.

2. The metal nanoparticles according to claim 1, being metal nanoparticles or metal-coated nanoparticles.

3. The metal nanoparticles according to claim 1, wherein the metal is gold.

4. The metal nanoparticles according to claim 1, wherein the compound switches its charge from negative under a neutral or alkaline environment to positive under an acidic environment.

5. The metal nanoparticles according to claim 1, wherein the compound is bonded to the ligand of the metal nanoparticles.

6. A method for preparing pH-sensitive metal nanoparticles comprising bonding a pH-sensitive compound to the surfaces of metal nanoparticles, wherein the charge of the compound changes depending on pH and is represented by the following chemical formula I:

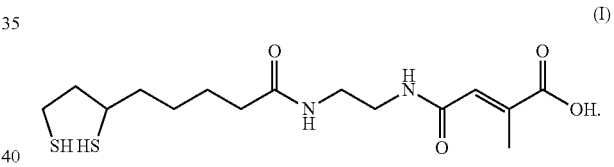

7. The method according to claim 6, wherein the metal nanoparticles are gold nanoparticles or gold-coated nanoparticles.

8. The method according to claim 6, wherein the compound is bonded to the metal nanoparticle by ligand substitution.

9. The method according to claim 8, wherein the surfaces of the metal nanoparticles are stabilized with citrate.

10. A method for destroying abnormal cells, comprising:
administering pH-sensitive metal nanoparticles of claim 1; allowing them to aggregate; and
irradiating the aggregated metal nanoparticles with light, thereby destroying the abnormal cells.

11. The method according to claim 10, wherein the abnormal cells are cells representing an acidic pH.

12. The method according to claim 10, wherein the abnormal cells are cancer cells.

13. The method according to claim 10, wherein the metal nanoparticles are introduced into the cells and form aggregations in the cells.

14. The method according to claim 10, wherein the metal nanoparticles are gold nanoparticles or gold-plated nanoparticles.

15. The method according to claim 10, wherein the charge of at least a portion of the compounds changes under an acidic pH environment.

16. The method according to claim 10, wherein the metal nanoparticles have an average diameter of 20 nm or less.

17. The method according to claim 10, wherein the light is a red or infrared light.

18. The method according to claim 17, wherein the light is a laser.

19. A pH-sensitive compound represented by the following chemical formula I or a salt thereof:

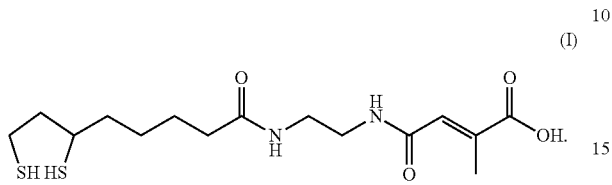

20. A sensor comprising the pH-sensitive nanoparticles of claim 1.

21. An image contrast agent, comprising the pH-sensitive nanoparticles of claim 1.

22. A reagent for diagnosis of cancer, comprising the pH-sensitive nanoparticles of claim 1.

23. A cancer therapeutic agent, comprising the pH-sensitive nanoparticles of claim 1.

* * * * *